United States Patent
Bluck et al.

(10) Patent No.: US 8,818,562 B2
(45) Date of Patent: Aug. 26, 2014

(54) SIMULATED FERMENTATION PROCESS

(75) Inventors: David Bluck, Yorba Linda, CA (US); Prashant R. Karbhari, Sugar Land, TX (US); Wen-Jing Lin, Sugar Land, TX (US)

(73) Assignee: Invensys Systems, Inc., Foxboro, MA (US)

( * ) Notice: Subject to any disclaimer, the term of this patent is extended or adjusted under 35 U.S.C. 154(b) by 106 days.

(21) Appl. No.: 13/153,393

(22) Filed: Jun. 4, 2011

(65) Prior Publication Data

US 2012/0310413 A1 Dec. 6, 2012

(51) Int. Cl.
*G06F 19/00* (2011.01)

(52) U.S. Cl.
USPC .......... 700/268; 700/266; 700/270; 700/271; 702/19; 436/24; 435/813; 435/161; 435/162; 435/163; 435/164; 435/165; 426/7; 426/11; 426/12; 426/13; 426/14; 426/15; 426/16; 426/18; 426/19; 426/20; 426/21; 426/22; 426/23; 426/24; 426/25; 426/26; 426/27; 426/28; 426/29; 426/30; 426/31

(58) Field of Classification Search
CPC .... G06F 17/5009; G05B 17/02; C12C 13/00; C12P 7/06; C12P 19/14; G06N 99/005

USPC .......... 700/266, 268, 270, 271; 426/7, 11–16, 426/18–31; 435/813, 161–165; 436/24; 702/19

See application file for complete search history.

(56) References Cited

U.S. PATENT DOCUMENTS

| | | | |
|---|---|---|---|
| 2003/0153059 A1* | 8/2003 | Pilkington et al. | 435/161 |
| 2008/0103747 A1* | 5/2008 | Macharia et al. | 703/11 |
| 2008/0167852 A1* | 7/2008 | Bartee et al. | 703/11 |
| 2009/0048816 A1* | 2/2009 | Srinivasa et al. | 703/11 |

OTHER PUBLICATIONS

Extended European Search report dated Jun. 5, 2013, for EP 12162570.1.
Written Opinion of the International Searching Authority dated Jun. 5, 2013 for EP 12162570.1.

* cited by examiner

*Primary Examiner* — Shogo Sasaki
(74) *Attorney, Agent, or Firm* — Edward S. Jamolowicz, Esq.

(57) ABSTRACT

A method of modeling a fermentation process comprises providing a first principles model of a fermentation process; determining the concentration of at least one substrate in a fermentation composition at a first time; and predicting the concentration of at least one component of the fermentation composition at a second time using the first principles model, wherein the second time is after the first time.

17 Claims, 6 Drawing Sheets

SIMULATED FERMENTATION PROCESS

CROSS-REFERENCE TO RELATED APPLICATIONS

None.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Beer and other brewed beverages are generally produced in a brewery within a given geographic location to limit the transportation costs and the amount of time required to deliver the beverages to a consumer. As a result, the brewing industry relies on many breweries throughout the world to produce a consistent product from one location to the next. Each brewery may use traditional techniques and local ingredients that can affect the final product. Traditional beer brewing techniques involve the use of a variety of feed components including a variety of grains, each of which can produce differences in the wort introduced to the fermentation process. Local supply differences throughout the world may further contribute to a variability in the feed composition used for each batch of beer brewed. Brewing has developed as an art, at least partly in response to the myriad feed components and varieties of beers produced. Current quality control checks are performed by trained brew masters who are experts in using tastings and sample fermentations to control the brewing program to achieve a desired result. However, some variability may occur from brewery to brewery and batch to batch. In some circumstances, a problem batch may be identified without any specific information on how the brewing program may be modified to achieve the desired final product. In addition, some variability may exist in the final products due to the differences between brew masters within a brewery or from brewery to brewery. All of these differences may contribute to the variability of a desired product throughout a particular region and/or the world.

SUMMARY

In an embodiment, a method of modeling a fermentation process comprises providing a first principles model of a fermentation process; determining the concentration of at least one substrate in a fermentation composition at a first time; and predicting the concentration of at least one component of the fermentation composition at a second time using the first principles model, wherein the second time is after the first time.

In an embodiment, a method of modeling a fermentation process comprises providing a first principles model of a fermentation process; determining the concentration of at least one substrate in a fermentation composition at a first time; predicting the concentration of at least one component of the fermentation composition at a second time using the first principles model, wherein the second time is after the first time; adjusting, by a control system, an operating parameter of the fermentation process in response to the predicted concentration varying from a target concentration by more than a threshold amount.

In an embodiment, a computer implemented system for implementing a fermentation simulation tool comprises at least one processor; a user interface; a memory comprising a non-transitory computer readable medium storing a first principles fermentation simulation tool, wherein the first principles fermentation simulation tool, when executed by the processor, configures the processor to: receive the concentration of at least one substrate in a fermentation composition at a first time; predict the concentration of at least one component of the fermentation composition at a second time using a first principles model of a fermentation process, wherein the second time is after the first time; and display the predicted concentration via the user interface.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
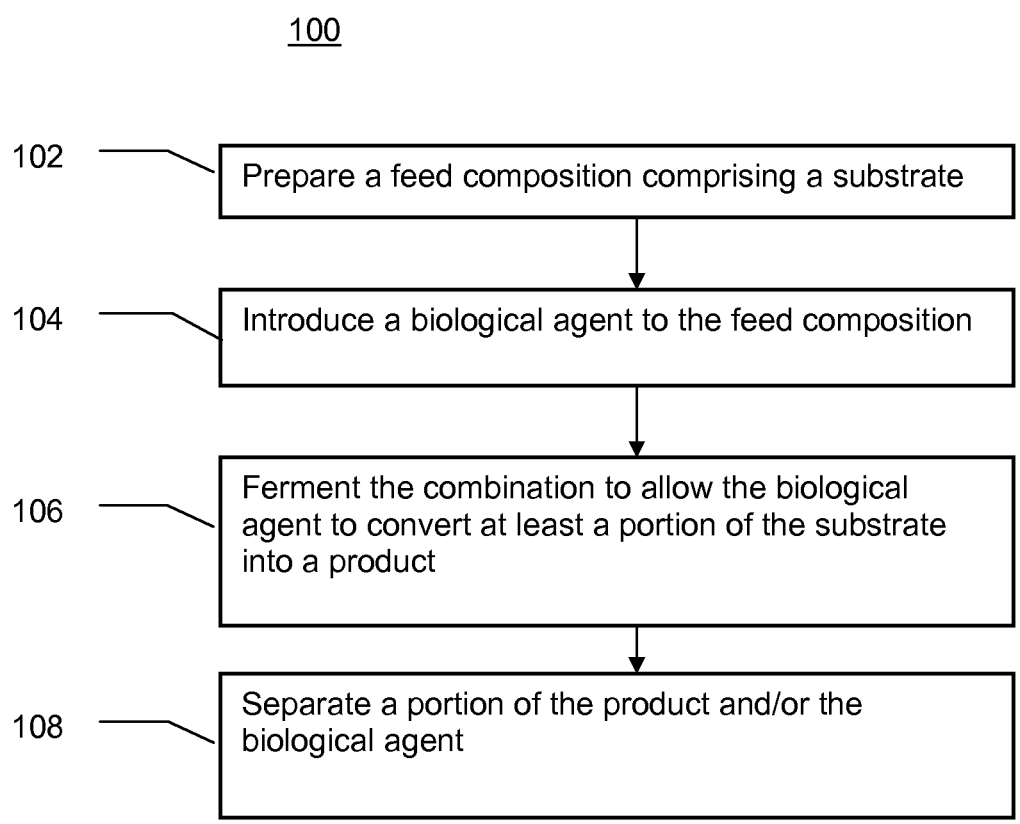
FIG. 1 is an illustration of a flow chart of an embodiment of a fermentation process.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The present disclosure provides a method of simulating a fermentation process using a first principles approach. Fermentation is a complex biochemical process involving one or more biologic agents and a variety of feed components that may be consumed by the various biologic agents at different rates. The feed components (e.g., the amount of sugar, protein, etc.) may be derived from naturally occurring sources (e.g., agricultural products) resulting in variability of the feed composition, such as when various grains are used in a beer fermentation process. For example, a feed composition comprising an agricultural product may vary from harvest to harvest due to non-uniformity in agricultural growing conditions such as the amount of water, sun, and growing temperatures, all of which can affect the feed composition. The variability is compounded when the feed comprises a combination of two or more agricultural products, each with individual variabilities in the amount of each component. Multiple side reactions, both desirable and undesirable, can occur during a fermentation process. Further, all of the components including the biologic agent, the feed composition, and the produced products can affect the various chemical processes occurring in the fermentation. All of these events may make it difficult to achieve a consistent and/or predictable product from the fermentation process.

A first principles approach may be used to model a desired fermentation process. While the reactions are complex, the processes can be modeled using parameters that can be fitted using experimentally obtained data. The models may be applied outside the range for which data is available since the fundamental mechanisms, such as the individual reactions, are being modeled. In addition, a feedback mechanism may be used to tune the first principles model during use to more accurately predict the results of the fermentation including the final fermentation composition. Once the models are provided and the parameters are determined using available data, a variety of results for the fermentation process can be predicted throughout the fermentation process. The results may be used to help identify when adjustments may be needed in the process. The models also may be used to verify the results of any proposed adjustments by simulating the effects of changes to the operating parameters. In addition, the predictions may be tied to a control system that may be used to implement a fully automated control system for automatically adjusting one or more parameters of the fermentation process. The resulting system may allow consistent results to be obtained more frequently from a process as complex as a fermentation process. In an embodiment, the results may be used to test and/or design additional fermentation process lines and/or entire fermentation processing facilities. These and other advantages will be discussed in more detail below.

As shown in FIG. 1, a fermentation process 100 generally begins with the preparation of a feed composition in step 102. The feed composition may comprise one or more components capable of being converted to one or more products in the fermentation process 100. As described in more detail herein, the feed composition may comprise one or more active components capable of being converted by a biologic agent such as sugars, polysaccharides, proteins, inorganic compounds (e.g., minerals), or other components useful during the life cycle of one or more biologic agents. The active components may be referred to as a substrate. The feed composition also may comprise one or more inactive components that may be useful in providing a suitable environment for the biologic agents or that may be present without effect on the overall system. For example, the active components used in a fermentation typically may be present in an aqueous solution to provide an appropriate environment for the biologic agents.

At step 104, a biologic agent may be introduced to the feed composition to form a fermentation composition. The biologic agent may be chosen to produce a desired product, and the feed composition may be prepared for the specific needs of the desired biologic agent. In an embodiment, suitable biologic agents may include, but are not limited to, a yeast, a bacteria, an algae, a genetically modified yeast, a genetically modified bacteria, a genetically modified algae, any other micro-organisms capable of producing a desired product, and any strain or strains thereof, and any combination thereof.

At step 106, the fermentation composition comprising the feed composition and the biologic agent may be fermented to allow the biologic agent to convert at least a portion of a substrate into one or more products. Within the fermentation process, several reactions and/or biological processes may be occurring. The main processes may comprise: 1) the growth of the biologic agent due to the consumption of one or more substrates in the feed composition, 2) the decrease in the concentration of the substrate based on the biological activity of the biologic agent, and 3) the increase in the concentration of one or more products produced by the biologic agent. Each process may involve a plurality of individual processes based on one or more variables. For example, the growth of the biologic agent may involve the growth of a plurality of biologic agents, each of which may consume one or more of the substrate components at different rates. These processes may be interrelated and create a dynamic process with respect to the concentration of the biologic agent, the substrate, and/or the product at any point during the fermentation process. Further, the conditions under which the fermentation is carried out may vary, resulting in a complex combination of components throughout the fermentation process. In an embodiment, the fermentation process may comprise a batch process, which comprises a process where substantially no mass crosses the process boundaries between the time the feed is charged and the time the product is removed and/or a semi batch process, which comprises a process where a limited amount of one or more components are allowed to cross the system boundaries between the time the feed is charged and the time the product is removed. For example, a beer fermentation process may be considered a semi batch process since at least a portion of the fermentation gases (e.g., carbon dioxide) are allowed to escape the system during the brewing process.

At step 108, a portion of the product and/or the biologic agent may be optionally separated. In an embodiment, the product may be desired in purified form, which may require some separation from the fermentation composition. In an embodiment, the biologic agent may be considered a product and may be separated.

The fermentation process 100 as shown in FIG. 1 may be used to produce a variety of products. In an embodiment, the fermentation process 100 may be used to produce products including, but not limited to, beer, wine, other fermented beverages, yogurt, other fermented food products, pharmaceuticals, and other products that may serve as intermediate components in the manufacturing of various commercial products (e.g., algae based hydrocarbons useful in the production of fuels, cosmetics, plastics, etc.). Additional steps and/or processes may be involved in different fermentation processes as would be known to one of ordinary skill in the art.

Figure 2:
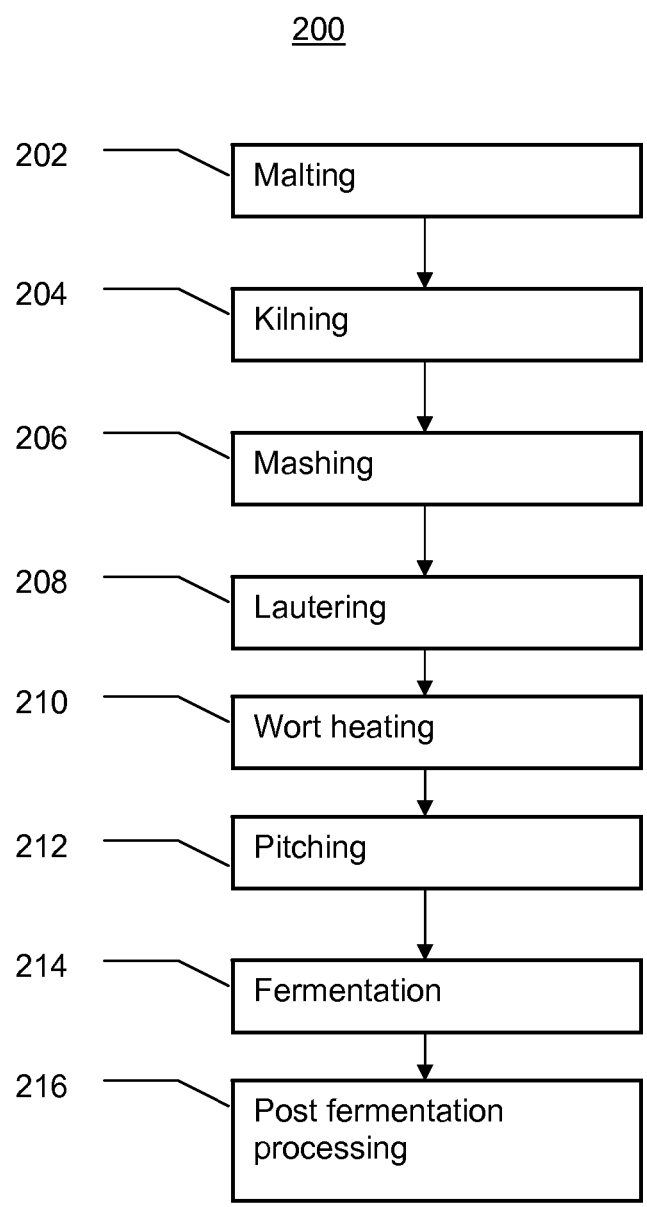
FIG. 2 is an illustration of a flow chart of an embodiment of a beer fermentation process.

In an embodiment, the fermentation process may be used to produce beer. A fermentation process 200 for producing beer is shown in FIG. 2. The beer fermentation process may begin with the preparation of a feed composition, which may be referred to as "wort" in the context of a beer fermentation process. The preparation of the wort may begin with "malting" one or more cereal grains such as corn, sorghum, maize, rice, rye, barley, and/or wheat in step 202. Malting may involve the germination of the grains by steeping and soaking in water to sprout the grains. During this process, several types of enzymes may be produced and/or released within the grains, including those that catalyze the conversion of starch into fermentable sugars.

The germinated grains may pass through a process referred to as "kilning" in step 204 in which the sprouted grains are dried and roasted to kill the sprouts and to provide the grain with roasted grain flavors and color. After kilning, the grains may be referred to as malted grains or simply "malt." The malt may be milled to a desired size to allow the components of the malted grains to be better extracted in water during the subsequent processes. The milled malt may be referred to as "grist."

The grist may then pass through a mashing process in step 206. Mashing may involve the mixing of the grist with water, to obtain a mixture referred to as a "mash." In order to activate the enzymes within the malt and/or any added enzymes, the mash may be heated. Mashing may be carried out at temperatures ranging from about 45° C. to about 75° C. During mashing, a variety of sugars such as oligosaccharides, disaccharides and monosaccharides can be generated by the enzymatic breakdown of complex carbohydrates, including mainly starch. Specific sugars may include, but are not limited to, dextrin, maltose, maltotriose, glucose, sucrose, fructose, and other polysaccharides. These sugars generally form at least a portion of the substrate for a beer brewing process and may provide the carbon and energy source for the biological activity of the biologic agent during the fermentation process.

The insoluble components remaining in the mixture, which may comprise the spent grains, may be removed in a process referred to as "lautering" in step 208. The remaining liquid and soluble components may be referred as the "wort." The lautering process may be carried out at a temperature of about 75° C. to about 100° C.

The wort may then be heated in step 210 and a variety of components may be added before or during the heating process to alter and/or enhance the flavor of the beer. The wort may be heated to a temperature sufficient to boil the composition and may be held at this temperature for a period of time. The boiling of the wort may aid in the pasteurization of the wort to eliminate competition for the added biologic agents during fermentation. During the boiling of the wort, any proteins or other solids that may affect the final quality of the beer may coagulate and be precipitated for removal from the wort. Once the bitter, aromatic, and flavoring compounds from herbs, such as hops, or herb extracts have been extracted, the remaining solids may be removed from the wort through filtering or other separation means.

A biologic agent then may be introduced into the wort in step 212. The wort may be cooled after the heating process to a temperature that is optimal for the biologic agents. The biologic agents useful for beer fermentation generally comprise a brewer's yeast, for example *saccharomyces cerevisiae*. The biologic agents may be added to the wort in a process referred to as "pitching." In an embodiment, the biologic agents may be added to the wort by spontaneous inoculation.

The combination of the biologic agent and the wort may then be fermented in a fermentation vessel to allow the biologic agents to convert at least a portion of the substrate (e.g., the sugars contained in the wort) into a product in step 214. Fermentation in the context of producing beer generally involves the incubation of the wort inoculated with the biologic agent. During fermentation, the sugars in the wort may be converted by the biologic agents into products including, but not limited to, carbon dioxide, ethanol, flavor components, and numerous other by-products. The fermentation process may proceed for a period of time ranging from days to weeks, depending on the type of beer being produced. In an embodiment, the fermentation process may proceed for about 9 to about 12 days before a product ready for further processing is produced.

During the beer fermentation process, a variety of parameters may be varied. The common parameters used to control the fermentation process include the dissolved oxygen content in the initial wort fed to the fermentation vessel, and the fermentation time, temperature, and pressure. The amount of dissolved oxygen in the initial wort can be controlled to some degree by the amount of air, which may be sterilized, sparged in the wort between the heating process and the pitching of the biologic agent. The remaining parameters may vary depending on the brewing process and the brewing program selected for each batch of wort to be fermented. For example, a typical brewing process may maintain the wort inoculated with the biologic agent at a first temperature for a first amount of time. At some point in the fermentation process, the temperature may be varied and again held at a second temperature for a second amount of time. This process may be repeated a desired number of times. The resulting "brewing program" or "brewing recipe" may be used to control the final content of the brewed composition.

The final brewed composition may comprise the products of the fermentation process. For beer fermentation, a variety of parameters may be used to characterize the brewed composition during and after the fermentation process including, but not limited to, sugar content, density, color, pH, alcohol content, real extract value, apparent extract value, diacetyl content, real degree of fermentation value, and any combination thereof. The sugar content in the initial wort may result, at least in part, from grains used to form the malt, the degree of malting, and the addition of any enzymes during mashing. The density of the fermentation solution is a product of the sugar concentration and the alcohol concentration, which varies throughout the fermentation process as sugars are converted to alcohol by the biologic agent. The color may result, at least in part, from the concentration of melanoidin compounds in the solution. The color may be varied by the selection of the malt composition, degree of kilning, and the duration of the wort heating process. The pH may be affected by acidification of the mash, products produced by the biologic agent, the choice of the biologic agent, and any additives used to control the pH of the water used in the process. Varying the pitching temperature, varying the fermentation temperature, and using additives (e.g., $CaSO_4$) may control the pH of the final brewed composition. The alcohol content may be affected by the choice of the biologic agent, the brewing recipe, and the length of the fermentation process.

Referring again to FIG. 2, once the fermentation process has reached a desired state, a variety of post fermentation processing may be carried out on the resulting liquid in step 216. Depending on the type of beer and the fermentation method used, the post-fermentation processes may include, but are not limited to, maturing the beer to further develop desirable flavors and aromas and/or reduce the levels of undesirable flavors and aromas; filtering the beer to remove the residual yeast and other turbidity-causing materials; treating the beer with an absorbent to remove specific compounds such as hydrophilic proteins or polyphenols; subsequently fermenting the beer (with or without addition of an extra carbon source); adding additional components to the beer such as herbs or herb extracts, and/or fruits or fruit extracts; carbonating the beer to increase the bubbly aspect of beer; pasteurizing and/or microfiltering the beer to enhance stability; and packaging the beer using a variety of processes including bottling, canning, and/or kegging.

In order to improve upon the traditional process of using tastings and brewing test batches, a first principles model may be used to simulate the fermentation process to allow for a prediction of the final brewed composition. A first principles model comprises one or more established or fundamental rules or laws of mathematical or scientific theory, which may be expressed as one or more mathematical equations. In an embodiment, a first principles model for a fermentation process comprises one or more rules or laws of scientific theory related to the chemical reactions occurring within the fermentation process. For example, the first principles model may comprise a set of equations that model the various reactions and/or processes occurring within a fermentation process. For example, the first principles model may comprise a set of equations that are based, at least in part, on the law of conservation of mass and/or on the law of conservation of energy.

The equations may comprise steady state and/or dynamic rate equations, depending on the types of simulations desired, the type of fermentation being modeled, and the type of data available for analysis. In an embodiment, a steady state model may be used to establish the final fermentation conditions, and a dynamic model may be used to analyze potential changes in the fermentation conditions. In an embodiment, the same model can be used for both steady-state and dynamic simulation. One or more constants (e.g., rate constants) may be used within the first principles equations and may be regressed using available data. Once the equations and constants are determined, the first principles model may be used to predict the state of the fermentation process having a set of operating conditions without further input, including at points that are beyond the data set used to determine the constants. The use of a first principles model may be distinguished from a purely empirical model in that the processes occurring within the fermentation process are being modeled, rather than merely establishing a correlation between the input parameters and the expected output parameters. In an embodiment, the use of a first principles model may allow for greater accuracy than an empirical model when simulating conditions beyond those for which data is available (i.e., when extrapolating results).

Simulation may involve the modeling of a system by representing the processes occurring within the system using one or more mathematical models and/or computations to project and/or to reveal the behavior of these systems as relevant parameters vary. For example, a simulation may use a first principles mathematical model of a fermentation process to project the behavior of the fermentation system as the concentrations of the various components in the fermentation composition vary over time, for example as feed products are consumed and/or transformed by biologic agents. In an embodiment, the mathematical computations may be implemented on a computer, as described in more detail below. The simulation may be carried out by calculating a sequence of states using the mathematical models, where the results for each state are used as an input into the calculation of the subsequent state at a desired incremental time period later. The simulation may be carried out faster than real-time and thus may be used to calculate the future state of a process at a desired time in the future. For example, the simulation may be used to predict the state of a process an hour, a day, or even weeks from the present.

In an embodiment, a first principles model for a general fermentation process may comprise equations and/or sets of equations grouped into sub-models to simulate the main reactions occurring during the fermentation process. The equations may comprise: 1) a growth model to account for the growth of the biologic agent due to the consumption of one or more substrates in the feed composition, 2) a substrate model to account for the decrease in the concentration of the substrate based on the biological activity of the biologic agent, and 3) a product model to account for the increase in the concentration of one or more products produced by the biologic agent. Each model may comprise one or more equations depending on the number of components being simulated in each sub-model. For example, if two biologically active components were present in a fermentation process, at least two equations may be used to simulate the growth of each biologic agent, which may occur at different rates depending on the substrate used in the feed composition. In an embodiment, rate based equations may be used along with a suitable rate constant or constants for each equation. The rate constant or rate constants may be regressed from available data, which may be obtained through preliminary testing using laboratory or production scale testing.

In an embodiment, the first principles model for a fermentation process may be tuned through the use of actual data obtained during the on-going fermentation process. During a fermentation process, a variety of conditions may result in the rate constants having a time dependency that may be difficult to model. For example, the biologic agent may pass through multiple generations during the fermentation process. Due to the complex nature of the reproductive process of microorganisms (e.g., due to mutations and/or adaptations), the activity of the biologic agent with respect to the various substrates may change during the fermentation process and/or over several fermentation processes when the biologic agent is reused. During the fermentation process, a plurality of actual samples may be taken at periodic intervals and the resulting concentrations and/or values compared to the concentrations and/or values predicted by the first principles model. Any discrepancies may be accounted for by adjusting the equations and/or the rate constants used in the equations. Thus, tuning the model through the use of feedback, which may be provided on a periodic basis and/or an aperiodic basis, may allow for improved accuracy of the model. In an embodiment, the time dependency of the rate constants may be mathematically modeled and included in the model equations to provide for an increased accuracy.

In order to demonstrate how a first principles model may be applied to a fermentation process, a description of a model for simulating the fermentation of beer is provided. However, it is expressly intended that similar models can be developed and implemented for other fermentation processes. In an embodiment, a first principles model for a beer fermentation process may comprise sub-models to simulate the main reactions occurring during the beer fermentation process. The equations may comprise: 1) a growth and bioaccumulation model to account for the growth and/or accumulation of the yeast, 2) a substrate model to account for the decrease in the concentration of the various substrates (e.g., one or more of the sugars), and 3) a product model to account for the change in the concentration of the products (e.g., alcohol, intermediate byproducts, etc.) in the composition. In order to aid in the understanding of the description of the models, Table 1 contains a list of the nomenclature used in the equations presented below.

TABLE 1

Nomenclature for Beer Fermentation Models

| Symbol | Description |
|---|---|
| Alc (v/v) | Ethanol (Alcohol) volume percentage (%) |
| E | Ethanol concentration (gmol/m$^3$) |
| $E_o$ | Initial ethanol concentration (gmol/m$^3$) |
| $E_{ki}$ | Arrhenius activation energy for Ki (cal/gmol) |
| $E_{mi}$ | Arrhenius activation energy for mi (cal/gmol) |
| $E_{kd}$ | Arrhenius activitation energy for Kd (cal/gmol) |
| G | Glycerol concentration (gmol/m$^3$) |
| $G_o$ | Initial glycerol concentration (gmol/m$^3$) |
| $I_i$ | Inhibition term for the $i^{th}$ sugar |
| $K_d$ | Specific biomass death rate (hr$^{-1}$) |
| $K_i$ | Michaelis constant for the $i^{th}$ sugar (gmol/m$^3$) |

TABLE 1-continued

Nomenclature for Beer Fermentation Models

| Symbol | Description |
|---|---|
| $K_{i0}$ | Arrhenius frequency factor for $K_i$ (gmol/m$^3$) |
| $K_x$ | Yeast growth inhibition constant (gmol/m$^3$)$^n$ |
| $K'_{ij}$ | Inhibition constant of sugar i due to sugar j |
| $m_i$ | Maximum velocity for the i$^{th}$ sugar (hr$^{-1}$) |
| $m_{i0}$ | Arrhenius frequency factor for $m_i$, (hr$^{-1}$) |
| $n_i$ | Number of sugars that inhibits the i$^{th}$ sugar consumption rate |
| $n_s$ | Number of sugars |
| R | Gas constant |
| $S_i$ | The i$^{th}$ sugar concentration (gmol/m$^3$) |
| $S_{i0}$ | The initial i$^{th}$ sugar concentration (gmol/m$^3$) |
| t | Time (hr) |
| T | Temperature (K) |
| X | Biomass concentration (gmol/m$^3$) |
| $X_0$ | Initial biomass concentration (gmol/m$^3$) |
| $X_D$ | Dead biomass concentration (gmol/m$^3$) |
| $Y_{ESi}$ | Yield coefficient (mols Ethanol/mol of the i$^{th}$ sugar) |
| $Y_{GSi}$ | Yield coefficient (mols glycerol/mol of the i$^{th}$ sugar) |
| $Y_{XSi}$ | Yield coefficient (mols biomass/mol of the i$^{th}$ sugar) |
| $\mu_i$ | Specific i$^{th}$ sugar uptake rate (hr$^{-1}$) |
| $\mu_L$ | Specific latent formation rate (hr$^{-1}$) |
| $\mu_x$ | Specific biomass growth rate (hr$^{-1}$) |

While the equations presented herein are expressed in standard mathematical forms, one of ordinary skill in the art would appreciate that some adjustments may be used to solve the equations using one or more mathematical methods and/or computer based numerical methods. For example, while the equations herein are articulated in terms of continuous time functions, in combination with the present disclosure, one skilled in the art would readily be able to adapt these continuous time equations to corresponding discrete time equations that may be more amenable to a computerized solution. Additionally, the equations may be adapted by multiplying through by one or more coefficients and/or additive offsets. In an embodiment, the growth model may be expressed as a rate based equation comprising rates for both the production of the biologic agent and the accumulation of biomass due to the dying biologic agent. The biologic agent production rate may be expressed as:

$$\frac{dX}{dt} = (\mu_x - K_d)X + \text{Latent term} \quad \text{(Eq. 1)}$$

where, $$\mu_x = \frac{K_x}{K_x + (X - X_0)^n} \sum_{i=1}^{n_s} Y_{XS_i} m_i \quad \text{(Eq. 2)}$$

The latent term may be represented by:

$$\frac{dX_L}{dt} = -\mu_L X_L \quad \text{(Eq. 3)}$$

where, $$\mu_L = \mu_{L0} e^{-\frac{E_{kL}}{RT}} \quad \text{(Eq. 4)}$$

The dead biologic agent may be described as a dead biomass with a production rate expressed as:

$$\frac{dX_D}{dt} = K_d X \quad \text{(Eq. 5)}$$

where, $$K_d = K_{d0} e^{-\frac{E_{kd}}{RT}} \quad \text{(Eq. 6)}$$

In an embodiment, the substrate model may be expressed as a set of rate based equations comprising rates for the decrease of each sugar being modeled. The substrate model accounting for the consumption of the i$^{th}$ sugar may be expressed as:

$$\frac{dS_i}{dt} = -\mu_i X \quad \text{(Eq. 7)}$$

where the i$^{th}$ sugar can be dextrin, maltotriose, maltose, glucose, fructose, or sucrose. In an embodiment, additional sugars, or a subset of these sugars may be used to model the sugar consumption in the fermentation composition. The specific growth rates $\mu_i$ can be expressed as:

$$\mu_i = \frac{m_i S_i}{K_i + S_i} I_i \quad \text{(Eq. 8)}$$

where the temperature dependency on the specific growth rates are expressed as:

$$m_i = m_{i0} e^{-\frac{E_{mi}}{RT}} \quad \text{(Eq. 9)}$$

$$K_i = K_{i0} e^{-\frac{E_{ki}}{RT}} \quad \text{(Eq. 10)}$$

The inhibition term ($I_i$) of sugar i due to existence of other sugars may be expressed as:

$$I_i = \prod_{j=1}^{ni} \frac{K'_{ij} S_j}{K'_{ij} + S_j} \quad \text{(Eq. 11)}$$

where $n_i$ is number of sugars that impact sugar i.

The product model to account for the increase in the concentration of alcohol in the composition may be expressed as:

$$E = E_0 + \sum_{i=1}^{n_s} Y_{ES_i}(S_{i0} - S_i) \quad \text{(Eq. 12)}$$

Glycerol also may be produced as a reaction product during the beer fermentation process. The production of glycerol may be expressed as:

$$G = G_0 + \sum_{i=1}^{n_s} Y_{GS_i}(S_{i0} - S_i) \quad \text{(Eq. 13)}$$

The initial values for the parameters $X_0$, $S_{i0}$, $E_0$, and $G_0$ may be obtained through the use of experimental data, for example using laboratory scale data. In an embodiment, the parameters $X_0$, $S_{i0}$, $E_0$, and $G_0$ may be obtained through various measurement techniques. In an embodiment, the various concentrations may be obtained using a liquid chromatography techniques, and in some embodiments, the sugar concentrations may be measured using high performance liquid chromatography (HPLC). The remaining parameters including $K_X$, $m_{i0}$, $K_{i0}$, $E_{mi}$, $E_{ki}$, $E_{kd}$, $K_d$, $K'_{ij}$, and yield coefficients, $Y_{ESi}$, $Y_{XSi}$, $Y_{GSi}$, may be determined based on regression analysis (e.g., least squares fitting) of data for the concentrations of the sugars being modeled, glycerol, ethanol, and the temperature profile. For example, the following least squares criterion may be used to regress the remaining parameters:

$$\min \phi = \sum_{j=1}^{Nruns} \sum_{i=1}^{Npoints} \left[ \sum_{k=1}^{Nsugars} [\omega_{s,ijk}(S_{i,j,k,plant} - S_{i,j,k,calc})]^2 + \right.$$

$$\left. [\omega_{s,ij}(E_{i,j,plant} - E_{i,j,calc})]^2 + [\omega_{g,ij}(G_{i,j,plant} - G_{i,j,calc})]^2 \right] \quad \text{(Eq. 14)}$$

where ω are weighting factors. The differential equations with algebraic constraints (DAEs) (Eq. 1-Eq. 13) can be integrated using any known DAE solvers. For example, an Euler Explicit method may be used to solve the DAEs. When the problem to be solved is a non-linear regression with DAE constraints, commercial regression solvers are available. For example the optimization problem in equation 14 may be solved using the commercially available solver in Excel 2007 available from Microsoft Corporation of Redmond, Wash.

In an embodiment, the model may use regressed constants to predict the concentration of one or more of the sugars, biomass, ethanol, glycerol, and diacetyl, and/or the value of various parameters such as the color and the pH, at a desired point during the fermentation process. The predicted values may be used to calculate or derive additional parameters including the density (e.g., the specific gravity) and the inferential indices, including the apparent extract (AE), real extract (RE), and the real degree of fermentation (RDF).

In an embodiment, the density of the fermentation solution in the form of the specific gravity (SG) may be determined using the Redlich-Kister excess volume model. The equations may be expressed as:

$$v = v_{ideal} + v^E \quad \text{(Eq. 15)}$$

$$v^E = \sum_{i=1}^{(ncomp-1)} \sum_{j=i+1}^{ncomp} v_{ij}^E \quad \text{(Eq. 16)}$$

$$v_{ideal} = \sum_{i=1}^{ncomp} x_i v_i \quad \text{(Eq. 17)}$$

$$\frac{Pv_{ij}^E}{RT} = x_i x_j [a_{ij} + b_{ij}(x_i - x_j) + c_{ij}(x_i - x_j)^2 + d_{ij}(x_i - x_j)^3 + e_{ij}(x_i - x_j)^4] \quad \text{(Eq. 18)}$$

where ncomp is the number of components, v is the molar volume of the mixture, $v_{ideal}$ is the ideal molar volume of the mixture, $v^E$ is the excess molar volume of the mixture, $v^E_{ij}$ is the excess molar volume of the i,j binary pair, P is the absolute pressure, R is the gas constant, T is the absolute temperature, $v_i$ is the pure component molar volume, $x_i$ is the mole fraction of component i, and $a_{ij}$, $b_{ij}$, $c_{ij}$, $d_{ij}$, and $e_{ij}$ are the binary interaction parameters regressed from experimental data. Equations 15 through 18 may be used to derive the specific gravity of the solution. The additional parameters then may be derived from the calculated ethanol concentration and the density. The following equations may be used to calculate the AE, the RE, and the RDF:

$$AE(w/w) = -616.868 + 1111.14(SG) - 630.272(SG)^2 + 135.997(SG)^3 \quad \text{(Eq. 19)}$$

$$RE = 0.385(Alc(v/v)) + 0.915(AE) \quad \text{(Eq. 20)}$$

$$RDF(\%) = 100(RE_0 - RE)/(RE_0) \quad \text{(Eq. 21)}$$

The coefficients of a third-order polynomial, relating AE in degrees Plato to specific gravity are obtained by linear regression of the tabulation of degrees Plato and specific gravities as described in the book by J. de Clerck, A TEXTBOOK OF BREWING, Vol. 1 (Chapman Hall, 1957).

The concentrations of the various components may be measured using laboratory techniques and equipment such as an HPLC at periodic intervals during the fermentation. The model then may be tuned by recalculating the constants using a new regression analysis based on the newly obtained data, alone or in combination with previously measured data. The tuning of the model may increase the accuracy of the simulation if any of the constants vary with fermentation time. In an embodiment, the tuning of the parameters may be a periodic process in which the model is tuned followed by predicting new values at a later time. The newly predicted results may be compared to another sample and retuned as necessary. In an embodiment, retuning the model may be conditioned on a predicted value varying from the measured value by a threshold amount.

In an embodiment, the first principles model may be used to predict various compositions throughout the fermentation process to achieve a fermentation composition during fermentation and/or at the completion of fermentation that satisfies certain specifications. The specifications may comprise concentrations of the various substrates and products, the amount of biomass produced, values of various parameters of the fermentation composition, and/or limitations on various by-products and/or contaminants. For a brewing process, the specifications may comprise concentrations of the various substrates (e.g., the sugars such as dextrin, maltotriose, maltose, glucose, fructose, or sucrose, proteins, inorganic compounds, etc.) and products (e.g., alcohol), the amount of biomass produced (e.g., the amount of yeast), values of various parameters of the fermentation composition (e.g., the density, the color, the pH, the real extract value, the apparent extract value, the real degree of fermentation value), and/or limitations on various by-products and/or contaminants (e.g., the diacetyl concentration, the glycol concentration, etc.). In an embodiment, the various specifications may be based on a desired product specification, contractual obligations, and/or various governmental regulations.

Figure 3:
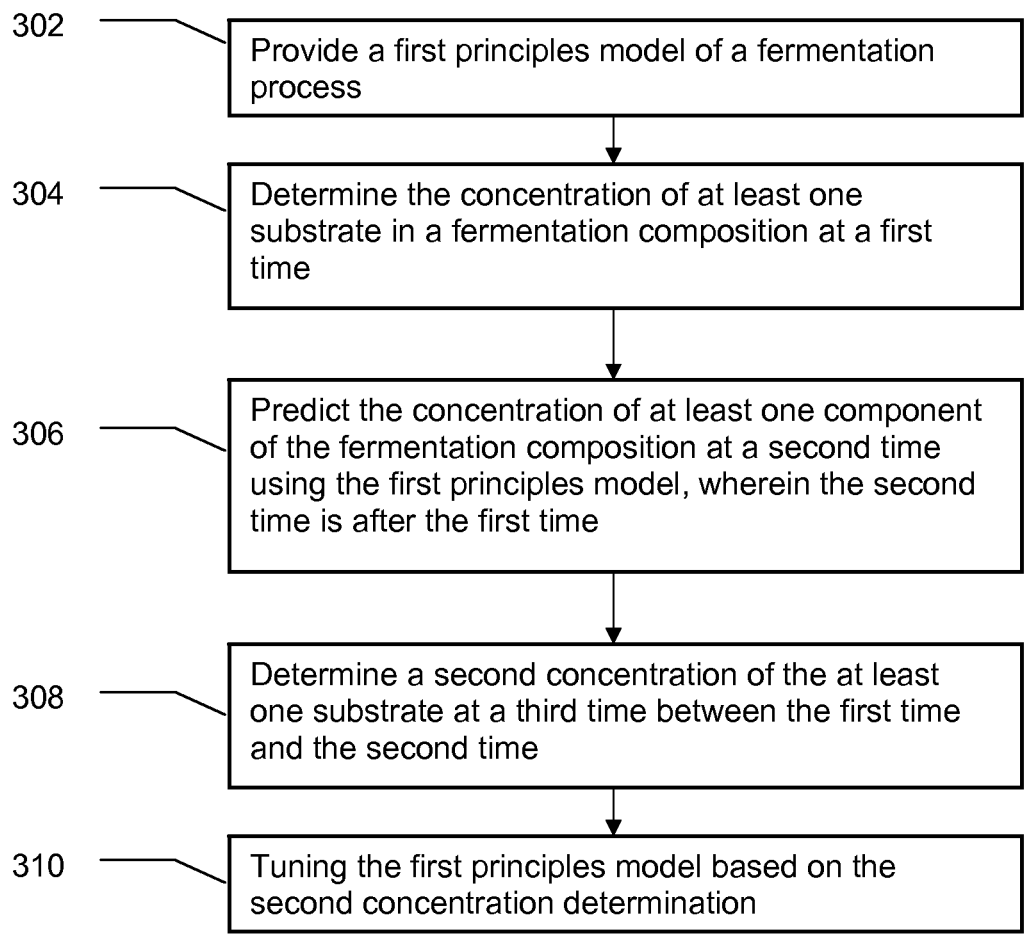
FIG. 3 is an illustration of a flow chart of an embodiment of a method for simulating a fermentation process.

As shown in FIG. 3, a method 300 for simulating a fermentation process may begin by providing a first principles model of a fermentation process at step 302. As discussed in more detail above, the fermentation process may be a beer fermentation process, a wine fermentation process, a yogurt fermentation process, and/or a pharmaceuticals fermentation process. In an embodiment, a fermentation process for any of these processes generally may comprise preparing a feed composition comprising at least one substrate, introducing a biologic agent to the feed composition to form the fermentation composition, and fermenting the fermentation composition to convert at least a portion of the substrate into at least one product. The corresponding first principles model of the fermentation process then may comprise one or more sub-models and/or equations to account for the individual processes occurring with the fermentation process. For example, the first principles model may include a growth model to account for the growth and/or accumulation of the biologic agent, a substrate model to account for the decrease in the concentration of the substrate, and/or a product model to account for the increase in the concentration of the at least one product. The first principles model may comprise a dynamic model and/or a steady-state model. In an embodiment, the first principles model may comprise one or more rate based equations with rate constants or other parameters derived from measured data, for example data obtained using laboratory scale and/or production scale testing.

In step 304, the concentration of at least one substrate in the fermentation composition may be determined at a first time. In an embodiment, the first time is the initial time at which the biologic agent is combined with the feed composition, for example at or near the time the yeast is pitched in a beer fermentation process. In an embodiment, a sample of the feed composition may be taken immediately prior to introducing the biologic agent to ensure that the initial concentrations of the substrate can be measured without being affected by any action of the biologic agent. For example in a beer fermentation process, a sample may be withdrawn as the wort is transferred from the heating process to the fermentation vessel. In this embodiment, the first time represents the initial point in time at which the biologic agent is combined with the feed composition even if the sample is taken at a time prior to the formation of the fermentation composition since the concentration of the substrate will not significantly change until the biologic agent is combined with the feed composition. In an embodiment, the first time may be any other time at which the concentration of at least one substrate is determined in the fermentation composition, which may depend on the number of times the fermentation composition is tested during the fermentation process. In an embodiment, the concentration of the substrate, or any other component of the fermentation composition, may be periodically tested every 12 hours, every day, every 2 days, every 3 days, and/or every 4 days. In an embodiment, the concentration of the substrate, or any other component of the fermentation composition, may be tested using a plurality of periodic testing phases. For example, the concentration of the substrate or any other component of the fermentation composition may be tested during days 1, 2, 3, and then tested every other day for the remainder of the fermentation process. In another embodiment, the concentration of the substrate, or any other component of the fermentation composition may be tested aperiodically. In an embodiment, the concentration of a plurality of substrate components may be determined at a first time. For example, two or more of the sugars forming the substrate may be measured and their concentrations determined at the first time.

The concentration of the substrate may be determined using a number of techniques. In an embodiment, a sample of the fermentation composition may be withdrawn from the fermentation composition and tested using standard laboratory techniques and equipment. For example an HPLC device may be used to determine the concentration of one or more sugars in the fermentation composition during a beer fermentation process. Additional suitable testing means may be used depending on the components being measured.

As shown in FIG. 3, the concentration of at least one component of the fermentation composition may be predicted using the first principles model at a second time at step 306. The component may comprise a biologic agent, a substrate, and/or a product. The second time is any point after the first time, including at the completion of fermentation. In an embodiment, a beer fermentation process may take from about 9 to about 12 days to complete, and the second time may be any time period up to the completion of the beer fermentation process. In an embodiment, the second time may be at any time up to and including packaging. In an embodiment, the second time may be any time up to and including a consumption date of the fermentation composition. Depending on the specific first principles model and/or equations used, the concentration of at least one component in the fermentation composition may be periodically predicted throughout the fermentation process. For example, a rate based equation may be used with a chosen time period to predict the concentration of at least one component, such as one or more sugars, throughout the fermentation process. In an embodiment, the time period may be any time period sufficient to predict the concentration of at least one component. In an embodiment of a beer fermentation process, the first principles model may be used to predict the concentration of one or more sugars every 12-24 seconds, for example every 18 seconds, throughout the fermentation process. In another embodiment of a beer fermentation process, the first principles model may be used to predict the concentration of one or more sugars at a different time step or time interval. In an embodiment, the first principles model may be used to predict a final concentration or value at the end of the fermentation process of a variety of parameters including, but not limited to, a sugar content, a density, a color, a pH, an alcohol content, a real extract value, an apparent extract value, a real degree of fermentation value, and any combination thereof. In an embodiment, the first principles model may be used to predict the concentration of two or more components at a second time. For example, all of the modeled sugars may be predicted along with a product concentration (e.g., the alcohol concentration) at the second time.

In the method 300, an optional tuning process may be employed. At step 308 a second concentration of the at least one substrate may be determined at a third time between the first time and the second time. In an embodiment, second concentrations of a plurality of substrates may be determined at the third time and used in the tuning process. At step 310, the first principles model may be tuned based on the second concentration determination. In an embodiment, tuning may comprise regressing at least one parameter of the first principles model using the second concentration determined at the third time. The concentration of the component of the fermentation composition then may be predicted at the second time using the first principles model with the updated parameter. Tuning may allow for an increased accuracy of the parameters of the first principles model. For example, any changes in the activity of the biologic agent with respect to the substrate may be accounted for by regressing the parameters used in the first principles model, including any sub-models, using the second concentration, alone or in combination with the previous concentration data.

The knowledge of the predicted values of at least one component of the fermentation composition throughout the fermentation process and at the end of the fermentation process may allow for proper planning for the use of the fermentation composition and/or products at the end of fermentation. The use of the first principles model may allow for the concentrations of the various components to be predicted without any additional inputs other than the initial composition of at least one component of the fermentation composition. When a predicted value for a concentration of one or more of the components of the fermentation composition indicates a problem (e.g., a final fermentation composition that does not meet one or more desired thresholds) with the fermentation process, corrective action may be taken to produce a final fermentation composition that meets acceptable thresholds. In a beer fermentation embodiment, the use of a first principles model may allow faster and more accurate predictions than traditional ideal brewing tests, which may take several days. Further, the use of the prediction of the concentrations throughout the brewing process and at the end of brewing may provide a more consistent product than can be achieved through the use of traditional testing alone.

Figure 4:
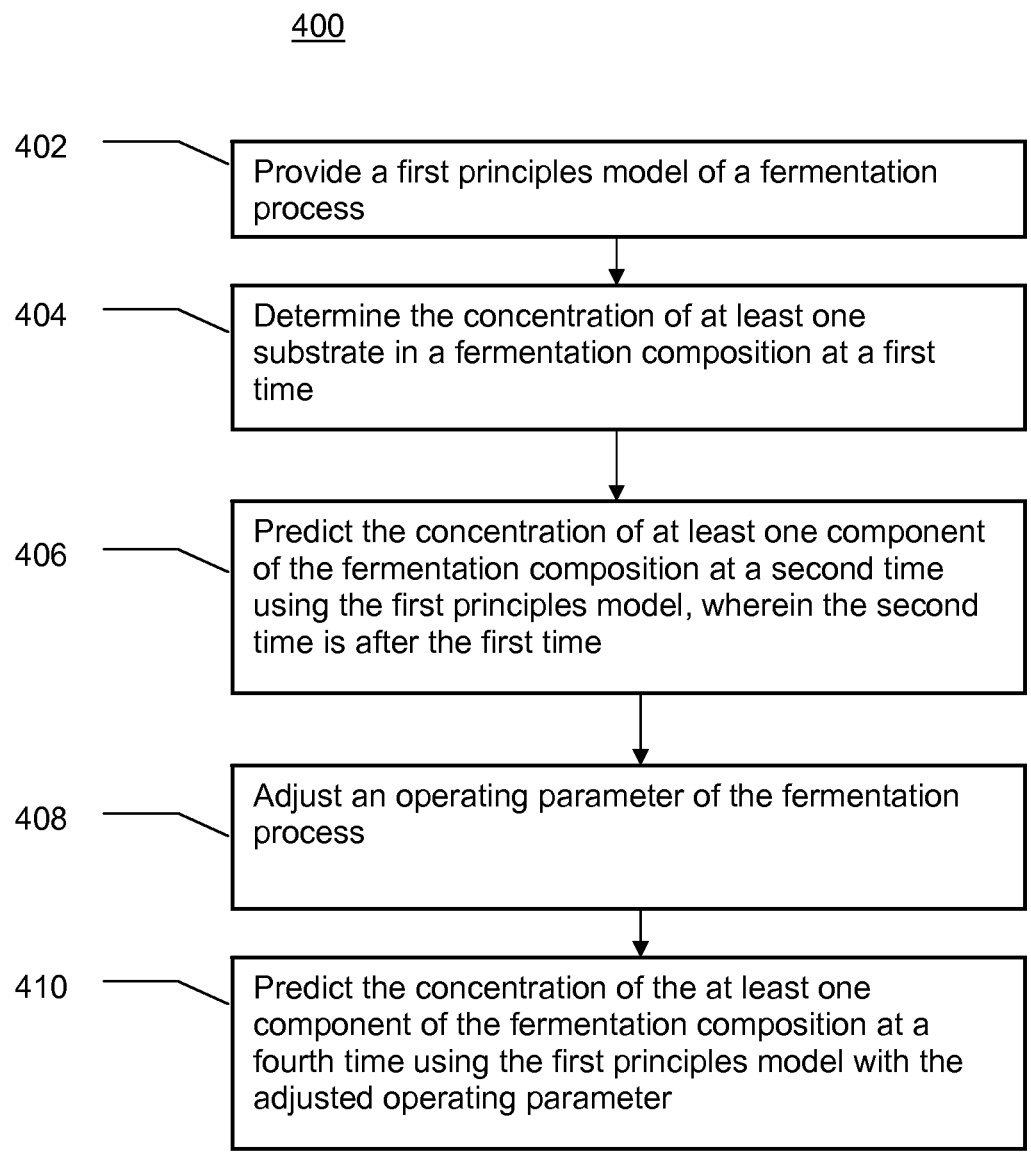
FIG. 4 is an illustration of a flow chart of another embodiment of a method for simulating a fermentation process.

As shown in FIG. 4, another method 400 for simulating a fermentation process may start with providing a first principles model of a fermentation process at step 402. At step 404, the concentration of at least one substrate in a fermentation composition may be determined at a first time. The concentration may be determined using any of the methods and/or techniques described herein. At step 406, the concentration of at least one component of the fermentation composition may be predicted at a second time, which is any time after the first time, using the first principles model. At step 408, an operating parameter of the fermentation process may be adjusted. In an embodiment, an operator may adjust one or more operating parameters based on the predicted concentration at the second time. The operating parameter may be any operating parameter that affects the fermentation process including, but not limited to, the dissolved oxygen content in an initial wort feed, a fermentation time, a fermentation temperature, and a fermentation pressure. At step 410, the concentration of the at least one component of the fermentation composition may be predicted at a fourth time using the first principles model with the adjusted operating parameter. In an embodiment, the fourth time may be the same as or different than the second time.

The knowledge of the predicted values of at least one component of the fermentation composition throughout the fermentation process and at the end of the fermentation process may allow an operator to test one or more adjustment scenarios. For example, an operator may plan on making an adjustment to a fermentation program and allow the first principles model to predict the results throughout the fermentation process, including the concentration of the various components in the final fermentation composition. This method may allow an operator to more accurately adjust the process to achieve a desired final fermentation composition. The ability to test the various adjustment scenarios also may allow a broader range of feed compositions to be used. Should a non-typical feed composition be used, the first principles model may allow an operator to adjust the fermentation program to achieve a desired final fermentation composition, even if the feed composition previously has not been used. Since most fermentation processes may incorporate a variety of components into the feed composition, this may allow some flexibility in formulating the feed composition without the need to run laboratory experiments to verify that the particular feed mixture will produce the desired result. In an embodiment, the ability to predict the concentration of at least one component of the fermentation composition may be used to test and/or develop additional fermentation processes. In an embodiment, the simulation may be used to test and/or design new fermentation process facilities, such as a new brewery in a location where local ingredients can be tested prior to design and/or construction of the facility.

Figure 5:
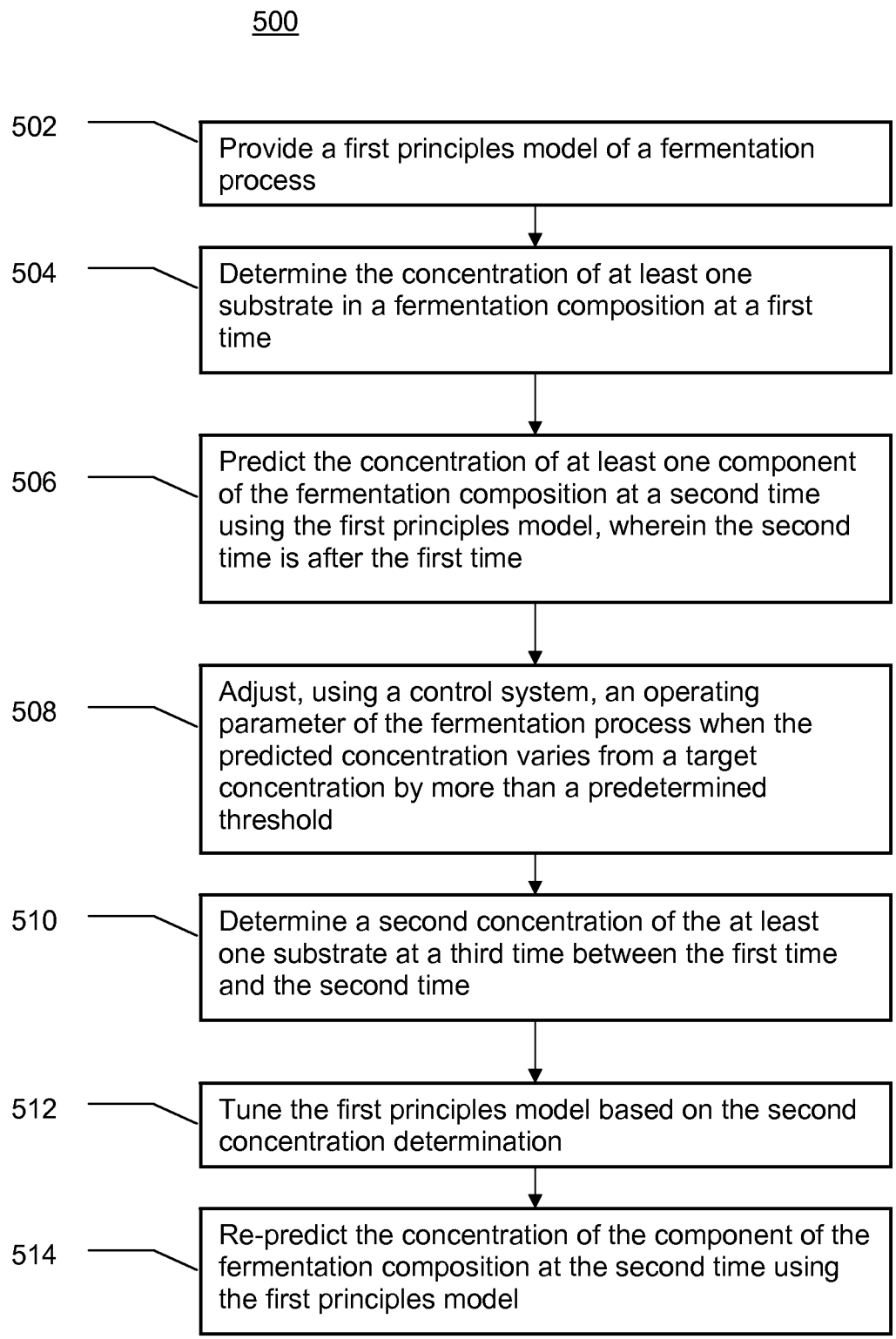
FIG. 5 is an illustration of a flow chart of still another embodiment of a method for simulating a fermentation process.

As shown in FIG. 5, another method 500 for simulating a fermentation process may start with providing a first principles model of a fermentation process at step 502. At step 504, the concentration of at least one substrate in a fermentation composition may be determined at a first time. The concentration may be determined using any of the methods and/or techniques described herein. At step 506, the concentration of at least one component of the fermentation composition may be predicted at a second time, which is any time after the first time, using the first principles model. At step 508, a control system may adjust an operating parameter of the fermentation process when the predicted concentration varies from a target concentration by more than a predetermined threshold. A control system may comprise components allowing one or more parameters of the fermentation process to be adjusted based on a desired setpoint. The operating parameter may be any operating parameter that affects the fermentation process including, but not limited to, the dissolved oxygen content in an initial wort feed, a fermentation time, a fermentation temperature, and a fermentation pressure. Steps 506 and 508 may be repeated at periodic intervals during the fermentation process to allow the control system to produce a desired final fermentation composition.

A tuning procedure may be carried out during the fermentation process 500. At step 510, a second concentration of the at least one substrate may be determined at a third time between the first time and the second time. The first principles model may be tuned based on the second concentration determination at step 512. The concentration of the component of the fermentation composition then may be re-predicted using the tuned first principles model at step 514.

The use of a method comprising a control system may promote increased automation of the fermentation process. This process may allow for the use of a wide variety of feeds used to form the feed composition while maintaining a consistent output within desired thresholds. The use of tuning may further increase the accuracy of the simulation and resulting final fermentation composition.

In an embodiment, the control system may receive measurements of fermentation process variables via a network providing communications throughout the plant and/or process, for example from sensors coupled to various components in the process plant such as a fermentation vessel. Sensors may measure the various process variables and may include temperature sensors, pressure sensors, and the like. Portions of the network may be provided by wired connections and/or links while other portions of the network may be provided by wireless connections and/or links. Based on the values determined from the first principles model in combination with the sensed fermentation process variables, the control system may determine control and/or command values. The control system may then transmit the control and/or command values via the network to a process controller, where the process controller may be coupled to one or more components of the fermentation process. For example, a process controller may vary the amount of heat or cooling fluid supplied to the fermentation process to control the fermentation temperature. The process controller may control one or more operating parameters (e.g., operating temperature, operating pressure, etc.) based on the control and/or command values received from the control system. The sensors may be used to provide feedback to the control system to indicate if further adjustments are needed. Portions of the control system may be implemented by a computer system. Computer systems are discussed further hereinafter.

In an embodiment, at least portions of the methods disclosed herein may be performed by a computer program executing on a computer system. In an embodiment, a first principles fermentation simulation tool may be stored on a memory comprising a non-transitory computer readable medium. The first principles fermentation simulation tool may be executed by at least one processor to configure the processor to perform the methods as described above. A system also may comprise a user interface to provide feedback to a user, and in some embodiments, allow for the input of data from various sources such as the determination of the concentration of the substrate in the fermentation composition.

The computer program may be used to configure one or more processors in a computer system to receive the concentration of at least one substrate in a fermentation composition at a first time; predict the concentration of at least one component of the fermentation composition at a second time using a first principles model of a fermentation process, wherein the second time is after the first time; and display the predicted concentration via the user interface. A tuning component also may be implemented using the simulation tool to configure the processor to receive a second concentration of the at least one substrate at a third time between the first time and the second time; and tune at least one parameter used by the first principles model based on the second concentration. In an embodiment, the simulation tool may be used to provide guidance on adjustments to the fermentation process by predicting the results of the adjustments. In this embodiment, the simulation tool may configure the processor to receive an adjusted operating parameter input for the fermentation process via the user interface; and predict the concentration of the at least one component of the fermentation composition at a fourth time using the first principles model with the adjusted operating parameter. In an embodiment, the simulation tool may be used in conjunction with a control system interface to automate the fermentation process. In this embodiment, the system also may comprise a control system interface, and the simulation tool may configure the processor to adjust at least one operating parameter of the fermentation process when the predicted concentration of the at least one component of the fermentation composition varies from a target concentration by more than a predetermined threshold.

Figure 6:
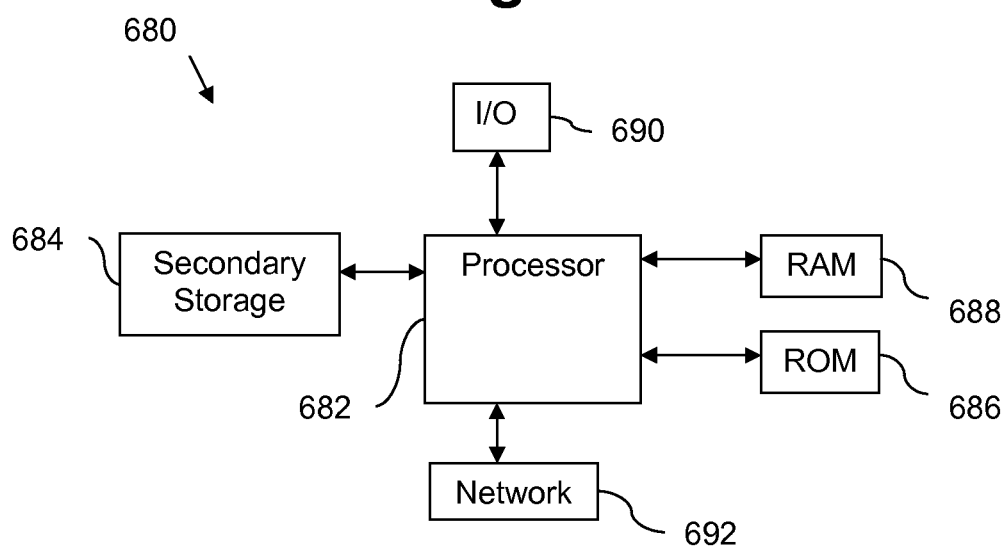
FIG. 6 is an illustrative example of a computer.

The control system described above may be implemented on any computer with sufficient processing power, memory resources, and network throughput capability to handle the necessary workload placed upon it. FIG. 6 illustrates a typical, computer system suitable for implementing one or more embodiments disclosed herein. The computer system 680 includes a processor 682 (which may be referred to as a central processor unit or CPU) that is in communication with memory devices including secondary storage 684, read only memory (ROM) 686, random access memory (RAM) 688, input/output (I/O) devices 690, and network connectivity devices 692. The processor may be implemented as one or more CPU chips.

It is understood that by programming and/or loading executable instructions onto the computer system 680, at least one of the CPU 682, the RAM 688, and the ROM 686 are changed, transforming the computer system 680 in part into a particular machine or apparatus having the novel functionality taught by the present disclosure. It is fundamental to the electrical engineering and software engineering arts that functionality that can be implemented by loading executable software into a computer can be converted to a hardware implementation by well known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

The secondary storage 684 is typically comprised of one or more disk drives or tape drives and is used for non-volatile storage of data and as an over-flow data storage device if RAM 688 is not large enough to hold all working data. Secondary storage 684 may be used to store programs which are loaded into RAM 688 when such programs are selected for execution. The ROM 686 is used to store instructions and perhaps data which are read during program execution. ROM 686 is a non-volatile memory device which typically has a small memory capacity relative to the larger memory capacity of secondary storage 684. The RAM 688 is used to store volatile data and perhaps to store instructions. Access to both ROM 686 and RAM 688 is typically faster than to secondary storage 684. The secondary storage 684, the RAM 688, and/or the ROM 686 may be referred to in some contexts as computer readable storage media and/or non-transitory computer readable media.

I/O devices 690 may include printers, video monitors, liquid crystal displays (LCDs), touch screen displays, keyboards, keypads, switches, dials, mice, track balls, voice recognizers, card readers, paper tape readers, or other well-known input devices.

The network connectivity devices 692 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards such as code division multiple access (CDMA), global system for mobile communications (GSM), long-term evolution (LTE), worldwide interoperability for microwave access (WiMAX), and/or other air interface protocol radio transceiver cards, and other well-known network devices. These network connectivity devices 692 may enable the processor 682 to communicate with the Internet or one or more intranets. With such a network connection, it is contemplated that the processor 682 might receive information from the network, or might output information to the network in the course of performing the above-described method steps. Such information, which is often represented as a sequence of instructions to be executed using processor 682, may be received from and outputted to the network, for example, in the form of a computer data signal embodied in a carrier wave.

Such information, which may include data or instructions to be executed using processor 682 for example, may be received from and outputted to the network, for example, in the form of a computer data baseband signal or signal embodied in a carrier wave. The baseband signal or signal embodied in the carrier wave generated by the network connectivity devices 692 may propagate in or on the surface of electrical conductors, in coaxial cables, in waveguides, in an optical conduit, for example an optical fiber, or in the air or free space. The information contained in the baseband signal or signal embedded in the carrier wave may be ordered according to different sequences, as may be desirable for either processing or generating the information or transmitting or receiving the information. The baseband signal or signal embedded in the carrier wave, or other types of signals currently used or hereafter developed, may be generated according to several methods well known to one skilled in the art. The baseband signal and/or signal embedded in the carrier wave may be referred to in some contexts as a transitory signal.

The processor 682 executes instructions, codes, computer programs, scripts which it accesses from hard disk, floppy disk, optical disk (these various disk based systems all may be considered secondary storage 684), ROM 686, RAM 688, or the network connectivity devices 692. While only one processor 682 is shown, multiple processors may be present. Thus, while instructions may be discussed as executed by a processor, the instructions may be executed simultaneously, serially, or otherwise executed by one or multiple processors. Instructions, codes, computer programs, scripts, and/or data that may be accessed from the secondary storage 684, for example, hard drives, floppy disks, optical disks, and/or other device, the ROM 686, and/or the RAM 688 may be referred to in some contexts as non-transitory instructions and/or non-transitory information.

In an embodiment, the computer system 680 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computer system 680 to provide the functionality of a number of servers that is not directly bound to the number of computers in the computer system 680. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In an embodiment, some or all of the functionality disclosed above may be provided as a computer program product. The computer program product may comprise one or more computer readable storage medium having computer usable program code embodied therein to implement the functionality disclosed above. The computer program product may comprise data structures, executable instructions, and other computer usable program code. The computer program product may be embodied in removable computer storage media and/or non-removable computer storage media. The removable computer readable storage medium may comprise, without limitation, a paper tape, a magnetic tape, magnetic disk, an optical disk, a solid state memory chip, for example analog magnetic tape, compact disk read only memory (CD-ROM) disks, floppy disks, jump drives, digital cards, multimedia cards, and others. The computer program product may be suitable for loading, by the computer system 680, at least portions of the contents of the computer program product to the secondary storage 684, to the ROM 686, to the RAM 688, and/or to other non-volatile memory and volatile memory of the computer system 680. The processor 682 may process the executable instructions and/or data structures in part by directly accessing the computer program product, for example by reading from a CD-ROM disk inserted into a disk drive peripheral of the computer system 680. Alternatively, the processor 682 may process the executable instructions and/or data structures by remotely accessing the computer program product, for example by downloading the executable instructions and/or data structures from a remote server through the network connectivity devices 692. The computer program product may comprise instructions that promote the loading and/or copying of data, data structures, files, and/or executable instructions to the secondary storage 684, to the ROM 686, to the RAM 688, and/or to other non-volatile memory and volatile memory of the computer system 680.

In some contexts, a baseband signal and/or a signal embodied in a carrier wave may be referred to as a transitory signal. In some contexts, the secondary storage 684, the ROM 686, and the RAM 688 may be referred to as a non-transitory computer readable medium or a computer readable storage media. A dynamic RAM embodiment of the RAM 688, likewise, may be referred to as a non-transitory computer readable medium in that while the dynamic RAM receives electrical power and is operated in accordance with its design, for example during a period of time during which the computer 680 is turned on and operational, the dynamic RAM stores information that is written to it. Similarly, the processor 682 may comprise an internal RAM, an internal ROM, a cache memory, and/or other internal non-transitory storage blocks, sections, or components that may be referred to in some contexts as non-transitory computer readable media or computer readable storage media.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A computer implemented system for a fermentation simulation tool for simulating a fermentation process, said system comprising:

at least one processor;

a memory comprising a non-transitory computer readable medium storing instructions for a first principles fermentation simulation tool defining a first principles model of a fermentation process, wherein instructions for the first principles model configure the processor to:
receive an initial concentration of at least one substrate in a fermentation composition at a first time;
predict a first concentration of at least one component of the fermentation composition at a second time using the first principles model of the fermentation process with the received initial concentration of the at least one substrate and, wherein the second time is after the first time;
adjust an operating parameter of the fermentation process based on the predicted first concentration at the second time; and
predict an additional concentration of the at least one component of the fermentation composition at an additional time after the second time using the first principles model with the adjusted operating parameter which is based on the predicted first concentration.

2. The system of claim 1, wherein the instructions for the first principles model configures the processor to predict a second concentration of the at least one substrate at a third time between the first time and the second time; and tune the first principles model based on the second concentration determination.

3. The system of claim 2, wherein the instructions for the first principles model configures the processor to predict by regression analysis at least one parameter of the first principles model using the second concentration determined at the third time; and predict the concentration of the at least one component of the fermentation composition at the second time using the first principles model with the at least one predicted parameter from the second concentration determined at the third time.

4. The system of claim 1, wherein the operating parameter comprises at least one parameter selected from the group consisting of: dissolved oxygen content in an initial wort feed, fermentation time, fermentation temperature, and fermentation pressure.

5. The system of claim 1, wherein the fermentation process comprises: preparing a feed composition comprising the at least one substrate; introducing a biologic agent to the feed composition to form the fermentation composition; and fermenting the fermentation composition to convert at least a portion of the substrate into at least one product.

6. The system of claim 1, wherein the fermentation process comprises a beer fermentation process, a wine fermentation process, a yogurt fermentation process, or a pharmaceuticals fermentation process.

7. The system of claim 1, wherein the instructions for the first principles model configures the processor to predict a final value of the operating parameter at the end of the fermentation process based at least in part on the first principles model, wherein the operating parameter comprises at least one parameter selected from the group consisting of: a sugar concentration, a density, a color, a pH, an alcohol concentration, a real extract value, an apparent extract value, a real degree of fermentation value, and any combination thereof.

8. The system of claim 1, wherein the first principles model includes a plurality of sub-models comprising: a growth model to account for the growth of a biologic agent, a substrate model to account for the decrease in the concentration of the substrate, and a product model to account for the increase in the concentration of the at least one product of the fermentation process.

9. The system of claim 1, wherein the substrate comprises a sugar, a polysaccharide, a protein, an inorganic compound, or any combination thereof.

10. The system of claim 1, wherein the component comprises a biologic agent, the substrate, an additional substrate, or a fermentation product.

11. A computer implemented system for implementing a fermentation simulation tool comprising:
at least one processor;
a memory comprising a non-transitory computer readable medium storing a first principles fermentation simulation tool defining a first principles model for a fermentation process, wherein the first principles fermentation simulation tool configures the processor to:
receive an initial concentration of at least one substrate in a fermentation composition at a first time;
predict a first concentration of at least one component of the fermentation composition at a second time using the first principles model of the fermentation process with the received initial concentration of the at least one substrate, wherein the second time is after the first time;
predict an additional concentration of at least one component of the fermentation composition at a time after the second time using the first principles model with the predicted first concentration of the at least one component;
display on a user interface the predicted additional concentration; and
adjust an operating parameter of the fermentation process in response to input provided by an user via the user interface.

12. The system of claim 11, wherein the first principles fermentation simulation tool further configures the processor to: receive a second concentration of the at least one substrate at a third time between the first time and the second time; and tune at least one parameter used by the first principles model based on the second concentration.

13. A computer implemented system for implementing a fermentation simulation tool comprising:
at least one processor;
a user interface;
a memory comprising a non-transitory computer readable medium storing a first principles fermentation simulation tool defining a first principles model for a fermentation process, wherein the first principles fermentation simulation tool configures the processor to:
receive an initial concentration of at least one substrate in a fermentation composition at a first time;
predict a first concentration of at least one component of the fermentation composition at a second time using the first principles model of the fermentation process with the received initial concentration of the at least one substrate, wherein the second time is after the first time;
receive an adjusted operating parameter input for the fermentation process via the user interface;
predict a new concentration of the at least one component of the fermentation composition at a time after the second time using the first principles model with the adjusted operating parameter;
display on the user interface the predicted new concentration; and
adjust an operating parameter of the fermentation process in response to input provided by an user via the user interface.

14. The system of claim 11, further comprising a control system interface configured to adjust one or more operating parameters of the fermentation process, and wherein the first principles fermentation simulation tool further configures the processor to: adjust at least one operating parameter of the fermentation process when the first or the new predicted concentration of the at least one component of the fermentation composition varies from a target concentration by more than a predetermined threshold.

15. The system of claim 11 wherein the processor is configured to display the predicted first concentration via the user interface.

16. The system of claim 1 further comprising a user interface and wherein the processor is configured to display the predicted additional concentration via the user interface.

17. The system of claim 16 wherein the processor is configured to display the predicted first concentration via the user interface.

\* \* \* \* \*